12 # United States Patent [19]

Filipkowski et al.

[11] Patent Number: 6,166,238
[45] Date of Patent: Dec. 26, 2000

[54] HIGH PURITY ORGANOFUNCTIONAL ALKYLDIALKOXYSILANES

[75] Inventors: Michelle A. Filipkowski, Marietta, Ohio; Petty E. Herbert, Bethel, Conn.; Curtis L. Schilling, Jr.; Mark D. Westmeyer, both of Marietta, Ohio

[73] Assignee: Crompton Corporation, Conn.

[21] Appl. No.: 09/481,144

[22] Filed: Jan. 12, 2000

[51] Int. Cl.$^7$ ..................................................... C07F 7/08
[52] U.S. Cl. ........................................... 556/479; 549/215
[58] Field of Search .............................. 556/479; 549/215

[56] References Cited

U.S. PATENT DOCUMENTS

| | | | |
|---|---|---|---|
| 4,160,775 | 7/1979 | Schilling, Jr. | 260/448.2 |
| 4,966,981 | 10/1990 | Takai et al. | 549/215 |
| 5,556,999 | 9/1996 | Yamada et al. | 556/401 |
| 5,559,264 | 9/1996 | Bowman et al. | 556/479 |
| 5,646,325 | 7/1997 | Monkiewicz et al. | 556/440 |
| 5,986,124 | 11/1999 | Tachikawa et al. | 556/479 |
| 6,015,920 | 1/2000 | Schilling et al. | 556/479 |

OTHER PUBLICATIONS

Ryan, *Journal of American Chemical Society*, 84, 4730–4734 (1962).
Pleuddemann, et al, *Journal of American Chemical Society*, 81, 2632–2635 (1959).
Goodman, et al, *Journal Of American Chemical Society*, 79, 3073–3077 (1957).
*Chem.Abst.*, 82: 16884 (1975).
Speier, et al, *Journal of Organic Chemistry*, 30, pp. 1651–1652 (1965).
Belyakova, et al, *J. Gen. Chem. USSR*, 44, 1744–45 (1971).

*Primary Examiner*—Paul F. Shaver
*Attorney, Agent, or Firm*—Shirley S. Ma, Esq.

[57] ABSTRACT

A method is provided for preparing high purity organofunctional alkyldialkoxysilanes by reacting hydroalkyldialkoxysilanes with olefins wherein formation of undesired close-boiling by-products by an alkyl/alkoxy group exchange reaction is minimized.

14 Claims, No Drawings

HIGH PURITY ORGANOFUNCTIONAL ALKYLDIALKOXYSILANES

FIELD OF THE INVENTION

The present invention relates to processes for preparing said silanes via hydrosilation reactions between hydroalkyldialkoxyilanes and olefinic reactants, wherein heretofore unrecognized rearrangement reactions, which generate undesired, close-boiling by-products, are minimized.

BACKGROUND OF THE INVENTION

Organofunctional alkoxysilanes have established and broad utilities as coupling agents, adhesion promoters, or crosslinking agents in applications involving inorganic fillers and substrates, and organic polymers. Most of such organofunctional silanes in commercial use in terms of both volumes produced and breadth of applications have been trialkoxysilanes, i.e., having three reactive alkoxy groups attached to each silicon atom, in addition to one organofunctional group.

The chemistries leading to the related alkyldialkoxysilanes have also long been known, but these products have not achieved the same high level of commercial success and are not produced in similarly large commercial volumes. There are several reasons for these differences, and these differences are reflected in less efficient processes, lower yields, and higher prices for organofunctional alkyldialkoxysilanes, making them less accessible in the marketplace.

In Journal of the American Chemical Society, Vol. 81, pp. 2632–2635(1959), Plueddemann and Fanger report the respective reactions of dimethylethoxysilane, methyldiethoxysilane, and triethoxysilane with allyl glycidyl ether as giving single products in substantially quantitative yields without presenting purity data, while isomeric products were detected in a related hydrosilation of butadiene monoepoxide. In each case, the hydrosilyl reactant was added to the olefinic epoxide. In the same journal, Volume 79, pp. 3073–3077(1957), Goodman et al report the hydrosilations of vinyl ethyl ether, vinyl n-butyl ether, and allylidene diacetate with methyldiethoxysilane by adding the olefin to the silane.

When methyldiethoxysilane is treated with chloroplatinic acid under hydrosilation conditions, a hydrogen/alkoxy exchange reaction is reported, without alkyl/alkoxy exchange (Chemical Abstracts, Volume 82, abstr. 16884v (1975), in English as Journal of General Chemistry, USSR, Volume 44, pp. 1744–5(1974)). More recently, U.S. Patent No. 4,966,981 discloses hydrosilations of allyl glycidyl ether wherein added alcohol is used to attain high product purity by reducing the level of formation of internal adducts to the allyl group vs. the formation of desired terminal adducts. All examples are run by adding the SiH-containing reactant to a stoichiometric excess of the olefinic reactant.

The art discloses a methyl/trimethylsiloxy group exchange which occurs when internal olefins (2-hexene, cyclohexene) are hydrosilated with bis(trimethylsiloxy) methylsilane, $(Me_3SiO)_2MeSiH$. Speier et al report in Journal of Organic Chemistry, Volume 30, pp. 1651–2 (1965) that such hydrosilations are accompanied by a methylltrimethylsiloxy group exchange.

While hydrosilation reactions have been run by adding the olefinic reactant to the hydrosilane on trialkoxy silanes, that mode has not been used generally because of safety hazards. See, for example, U.S. Pat. Nos. 4,160,775 and 5,559,264.

There appears to be no known example of alkyl/alkoxy group exchange reaction occurring during hydrosilation reactions of hydroalkyldialkoxysilanes with olefins. Alkyl/alkoxy group exchange reactions have been reported for simple methylalkoxysilanes at high temperatures with strong base catalysts, but these involve neither hydroalkyldialkoxysilanes nor hydrosilatable olefins. See Ryan, Journal of the American Chemical Society, Volume 84, p. 4730(1962).

SUMMARY OF THE INVENTION

The present invention provides a method for preparing high purity organofunctional alkyldialkoxysilanes wherein the formation of undesired by-products from a previously unrecognized alkyl/alkoxy group exchange reaction is minimized. The process involves the addition of the alkyldialkoxy silane to the allylic species to affect the hydrosilation.

DETAILED DESCRIPTION OF THE INVENTION

The reactions of interest herein may be represented by the following general equation,

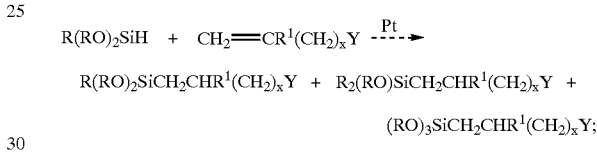

$$R(RO)_2SiCH_2CHR^1(CH_2)_xY + R_2(RO)SiCH_2CHR^1(CH_2)_xY +$$

$$(RO)_3SiCH_2CHR^1(CH_2)_xY;$$

wherein R is a lower alkyl group of one to four carbon atoms, $R^1$ is hydrogen or R, x is an integer of 1 to 15, and Y is R or a carbon-, oxygen-, nitrogen-, or sulfur-bonded functional group with the provisos that when x=1, Y is not a halogen and that x may be 0 when Y is a carbon-bonded functional group wherein the bonding carbon is also attached only to carbon or hydrogen atoms or Y is a silicon-bonded functional group. The major product is $R(RO)_2SiCH_2CHR^1(CH_2)_xY$, the exchange reaction products, $R_2(RO)SiCH_2CHR^1(CH_2)_xY$ and $(RO)_3SiCH_2CHR^1(CH_2)_xY$, are minor products. The olefinic compound, $CH_2=CR^1(CH_2)_xY$, also represents cyclic and linear olefins wherein the double bond is not in a terminal position, including olefins formed by isomerization of $CH_2=CR^1(CH_2)_xY$, as, for example, $CH_3CR^1=CH(CH_2)_{x-1}Y$, which normally accompanies hydrosilation.

The present invention is concerned primarily with the alkyl/alkoxy group exchange reaction, leading to the by-products $R_2(RO)SiCH_2CR^1(CH_2)_xY$ and $(RO)_3SiCH_2CR^1(CH_2)_xY$, plus their precursors, $R_2(RO)SiH$ and $(RO)_3SiH$, and processes for their minimizaton, such that the desired product, $R(RO)_2SiCH_2CR^1(CH_2),Y$, can be obtained in high purity, by routine purification means, as by distillation. Said high purity should be greater than 95%, with the content of the alkyl/alkoxy exchange reaction products being less than 1% combined total. As an added advantage, the processes of the present invention also allow use of lower molar excesses of the olefinic reactant, due to lowered degree of isomerization of said olefinic reactant during the hydrosilations.

The process is run preferably in a mode wherein the olefinic reactant, $CH_2=CR^1(CH_2)_xY$, is added to the hydroalkyldialkoxysilane reactant, $R(RO)_2SiH$, in the presence of a platinum-containing catalyst. Thus, the silane reactant would be in the stoichiometric excess in the reaction vessel, at the desired temperature level with the catalyst as the olefin is added to the the reactor, until about a stoichiometric equivalent of the olefin is added.

The hydroalkyldialkoxysilane reactant, $R(RO)_2SiH$, where R is a lower alkyl group of one to four carbon atoms and may be the same or different in a given molecule, includes compounds ranging from methyldimethoxysilane to butyldibutoxysilane, where butoxy- may be n-butoxy-, i-butoxy-, s-butoxy-, or t-butoxy-, but is preferably selected from the group of methyldimethoxysilane and methyldiethoxysilane. These silanes are generally made by reactions of methyldichlorosilane, $MeSiHCl_2$, with at least two molar equivalents of the corresponding alcohol.

The platinum-containing catalyst are well-known hydrosilation catalysts, namely solutions of or derived from chloroplatinic acid and platinum-olefin complexes including platinum-vinylsiloxane complexes. Various additives and promoters known in the art may be used with the platinum catalyst, depending on the olefinic reactant. Such additives and promoters may include acids such as acetic acid, bases such as triethylanrine or phenothiazine, alcohols, such as methanol or ethanol, inorganics such as sodium carbonate or potassium carbonate, where such additives or promoters are used to increase rates or minimize known side reactions. Acetic acid is a preferred additive for the hydrosilation processes of the present invention at a use level of 100 to 5000 parts per million by weight of the combined reactants. Solvents, which have the effect of lowering unit yields by occupying unit volume, may be used if desired, but are not a requisite feature of the present invention.

The olefinic reactant, $CH_2=CR^1(CH_2)_xY$, where $R^1$ is hydrogen or R as defined above, x is an integer of 1 to 15, and Y is R or a carbon-, oxygen-, nitrogen-, or sulfur-bonded functional group with the proviso, when x=1, Y cannot be a halogen and that x may be 0 when Y is a carbon-bonded functional group wherein the bonding carbon is also attached only to carbon or hydrogen atoms or Y is a silicon-bonded non-halo functional group, can be selected from a wide variety of functional olefins, including hydrocarbon olefins such as octene or vinylcyclohexene, and including functional olefins now in commercial use in hydrosilation processes. Examples of Y are thioethers, ethers, epoxides, carbamatos, isocyanatos, polyethers, amines and alkyls. Specific examples of Y are glycidoxy, 3,4-epoxycyclohexyl, methacryloxy, polyetheroxy, 4-hydroxy-3-methoxyphenyl, n-pentyl, and the like. The olefins thus include allyl esters, such as allyl methacrylate, allyl glycidyl ethers, other allylic ethers including allyl polyethers, allyl aromatics such as eugenol, the corresponding methallyl compounds, and olefins not represented by the general formula, including cycloolefins such as cyclohexene, non-terminal olefins such as tertiary-amylene and those formed by isomerization of $CH_2=CR^1(CH_2)_xY$, acetylene and substituted acetylenes, vinyl cycloalkene epoxides, and vinylic silanes including vinyltrialkoxysilanes. The commercially useful olefins are preferred, with allyl glycidyl ether being most preferred.

The ratio of olefinic reactant to hydroalkyldialkoxysilane reactant will generally be close to or greater than 1. It is generally preferred to use a molar excess of the olefinic reactant to ensure consumption of the silicon-bonded hydrogen groups, while allowing for side reactions which also consume the olefinic reactant, such as isomerization and reduction. A preferred ratio of olefinic reactant to hydroalkyldialkoxysilane reactant is 1.01 to 2, with 1.05 to 1.3 being most preferred. The processes of the present invention, performed by adding the olefinic reactant to the hydroalkyldialkoxysilane reactant, allow the ratio to be in the lower part of the range, i.e., 1.05 to 1.15. It is noteworthy that the latter lower ratios appear to be unique to the hydroalkyldialkoxysilanes, and that consumption of all the SiH-containing reactant at such low ratios is not observed as generally with trialkoxysilanes, such as trimethoxysilane.

Reaction conditions are typical of those for commercially practiced hydrosilations except that the olefinic reactant is preferably added to the hydroalkyldialkoxysilane in the presence of the platinum catalyst. Reaction temperatures are elevated, in the range of 50 to 150° C., preferably 75 to 105° C., and most preferably 80–100° C. Platinum catalyst concentrations are in the range of 5–100 parts per million (ppm) of Pt by weight of the combined reactants, preferably in the range of 10–50 ppm, and most preferably in the range of 10–20 ppm. Reaction pressures are normally atmospheric, for convenience, although these reactions can be run at subatmospheric or superatmospheric pressures if the equipment is capable. Purification, as by distillation, is typically run under vacuum.

The processes of the present invention can be practiced in a variety of equipment suitable for the purpose of hydrosilation reactions ranging from small laboratory glassware through pilot scale to large production units. The only needs are for means of heating, cooling, maintenance of an inert atmosphere, preferably nitrogen, means for adequate agitation, means for introduction of reactants and catalyst in controlled fashion, and means for purifying the reaction products, as by distillation.

Whereas the exact scope of this invention is set forth in the appended claims, the following specific examples illustrate certain aspects of the present invention and, more particularly, point out various aspects of the method for evaluating same. However, the examples are set forth for illustrative purposes only and are not to be construed as limitations on the present invention. The abbreviations g, ml, mm, mol, ppm, μl, L, lb, kg, GC, and MS respectively represent gram, milliliter, millimeter, molar equivalent, parts per million, microliter, liter, pound, kilogram, gas chromatography, and mass spectrometry. All temperatures are reported in degrees Centigrade, and all reactions were run in standard laboratory glassware or pilot scale or production units at atmospheric pressure under an inert atmosphere of nitrogen, and all parts and percentages are by weight.

EXAMPLES

Comparative Example 1

Hydrosilation of Methyldiethoxysilane and Allyl Glycidyl Ether by Prior Art Addition To a 250 ml 4-neck round bottom flask, equipped with stir bar, thermocouple probe, condenser, addition funnel and nitrogen inlet/outlet, were added 70.8 g (0.62 mol) of allyl glycidyl ether (AGE). A 20% excess of the raw material was used in the preparation, as some isomerization of AGE occurs in the presence of heat and platinum catalyst. A solution of 10% chloroplatinic acid in ethanol (CPA, 78 μl, 15 ppm Pt) catalyst and 90 μl (650 ppm) of acetic acid were added to the AGE in the reaction vessel. The mixture was heated to 85° C. Methyldiethoxysilane (67.0 g, 0.52 mol), which had been charged to the addition funnel, was added drop-wise to the heated mixture at such a rate as to keep the pot temperature between 85–90° C. After silane addition completion (about 80 minutes), the reaction was heated at 85° C. for 30 minutes. GC Analysis showed, besides AGE and isomers, 81.1% of desired product, γ-glycidoxypropylmethyldiethoxysilane.

Also present were two unexpected scrambled products: γ-glycidoxypropyldimethyl(ethoxy)silane (1.10% by GC) and γ-glycidoxy-propyltriethoxysilane (1.24% by GC). GC-MS Data of the above mixture support the structures of the product and two scrambled side-products.

Example 1
Hydrosilation of Methyldiethoxysilane and Allyl Glycidyl Ether by Inverse Addition To the apparatus of Comparative Example 1 were added 67.0 g (0.52 mol) of methyldiethoxysilane, 78 μl (15 ppm Pt) of 10% CPA solution and 90 μl (650 ppm) of acetic acid. The mixture was heated to 85° C. AGE (70.8g, 20% excess at 0.62 mol), which had been charged to the addition funnel, was added drop-wise to the heated mixture at such a rate as to keep the pot temperature between 85–90° C. After AGE addition completion (approximately 80 minutes), the reaction was then heated at 85° C. for 30 minutes. GC analysis of the crude reaction mixture also showed complete conversion of the methyldiethoxysilane. GC analysis showed, besides AGE/isomers, 75.3% of desired product, γ-glycidoxypropylmethyldiethoxysilane. Again present, though in much smaller amounts, were the two side products γ-glycidoxypropyldimethyl(ethoxy)silane (0.16% by GC) and γ-glycidoxypropyl-triethoxysilane (0.36% by GC).

Example 2
Hydrosilation of Methyldiethoxysilane and 11% Excess Allyl Glycidyl Ether by Inverse Addition To the apparatus of Example 1 were added 67.0 g (0.52 mol) of methyldiethoxysilane, 78 μl (15 ppm Pt) of 10% CPA solution and 90 μl (650 ppm) of acetic acid. The mixture was heated to 85° C. Next, an 11% molar excess of AGE (64.0 g, 0.58 mol) was added drop-wise from an addition funnel to the heated mixture at such a rate as to keep the pot temperature between 85–90° C. After AGE addition completion (50 minutes), the reaction was heated at 85° C. for 30 minutes. GC analysis showed, besides AGE/isomers, 89.6% of desired product, γ-glycidoxypropylmethyldiethoxysilane. Present, although in smaller amounts, were the two scrambled products γ-glycidoxypropyldimethyl-(ethoxy)silane (0.29% by GC) and γ-glycidoxypropyltriethoxysilane (0.34% by GC).

Example 3
Hydrosilation of Methyldiethoxysilane and Allyl Glycidyl Ether at Larger Scale by Inverse Addition To a jacketed 50 L glass vessel equipped with agitator, thermocouple probe, condenser and nitrogen atmosphere were pressure charged 48.0 lb [21.8 kg] (50 lbs [22.7 kg]×96% purity, 162.8 mol) of methyldiethoxysilane from a 10 gallon Pope can. After addition of 10% CPA solution (20.0 ml or 15 ppm Pt) and acetic acid (25.0 ml or 550 ppm) through the handhole, the reactor was kept under nitrogen purge, sealed and heated to 85° C. Allyl glycidyl ether (49.0 lb [22.3 kg], using a 20 mole % excess of 195.4 mol) was introduced through a TEFLON line to the mixture in the 50 L reactor also from a pressurized Pope can. The AGE was added at such a rate as to keep the reaction temperature between 85 and 100° C. This resulted in a rate of about 20 lb [9.1 kg]/hr. After over 2.5 hr, the addition was complete and the kettle was cooled to 50° C. for sampling. GC analysis found the methyldiethoxysilane (0.04% remaining) to be almost completely converted to hydrosilation product. After a lites strip, the crude product was vacuum distilled at 123–133° C. (6.5–8.0 mm Hg) to yield 78.35 lb. (35.53 kg) of 98.3% pure material by GC. This is a percent conversion of 88.2%. Also present were the two scrambled products γ-glycidoxypropyldimethyl (ethoxy)silane (0.44% by GC) and γ-glycidoxypropyltriethoxysilane (0.37% by GC).

Example 4
Another Hydrosilation of Methyldiethoxysilane and Allyl Glycidyl Ether at Larger Scale by Inverse Addition Again, to the apparatus of Example 3 were pressure charged 49.6 lb [22.5 kg] (168.2 mol) of methyldiethoxysilane from a 10 gallon Pope can. After addition of the 20.0 g of CPA ethanol solution (15 ppm Pt) and 21.0 ml (460 ppm) of acetic acid through the handhole, the reactor was kept under nitrogen purge, sealed and heated to 85° C. Allyl glycidyl ether (50.6 lb [23 kg], 20 mole % excess or 210.8 mol) was added through a line to the mixture in the reactor from a pressurized can. The AGE was added at a rate that kept the reaction temperature between 85 and 95° C. After two hours, the addition was complete and the hydrosilation lites were stripped. The crude product was vacuum distilled at 104–121° C. (3–7 mm Hg) to yield 75.5 pounds (31.23 kg) of γ-glycidoxypropylmethyldiethoxysilane with an average purity of 99.0%. This represents a conversion of 82.3%. Again present were the silane scrambled products γ-glycidoxy-propyldimethyl(ethoxy) silane (0.39% by GC) and γ-glycidoxypropyltriethoxysilane (0.27% by GC).

Comparative Example 2
Hydrosilation of Methyldiethoxysilane and Allyi Glycidyl Ether in a Pilot Scale Reactor by Prior Art Addition Conditions To a jacketed Hastelloy-C reactor, equipped with agitator, temperature probe, condenser and nitrogen purge, were added 391 lb [177.7 kg] (1559 mol) of allyl glycidyl ether (AGE), followed by 151 ml (15 ppm Pt) of 10% CPA catalyst solution and 0.36 lb [164 g] (470 ppm) of acetic acid promoter. The reactor contents were heated to 80° C. Methyldiethoxysilane (370 lb [168.2 kg], 1255 mol) was metered in at such a rate as to keep the reactor temperature between 80–90° C. After completion of reaction, about 3.5 hours of silane addition and a one hour hold, a majority of the excess AGE/isomers were stripped to give a crude GC yield of 86.3% desired hydrosilation product. GC Analysis also showed 2.53% γ-glycidoxypropyldimethyl(ethoxy)silane and 2.95% γ-glycidoxypropyltriethoxysilane.

Example 5
Hydrosilation of Methyldiethoxysilane and Allyl Glycidyl Ether in a Pilot Scale Reactor by Inverse Addition To the reactor of Comparative Example 2 were added 370 lb [168.2 kg] (1255 mol) of methyldiethoxysilane, followed by 151 ml of 10% CPA catalyst solution (15 ppm) and 0.36 lb [164 g] (470 ppm) of acetic acid promoter. The reactor contents were heated to 80° C. AGE (390 lb [177.3 kg], 1559 mol) was added at a rate to keep the reactor temperature between 80–90° C. After completion of AGE addition (about 3.5 hours) and heating for one hour at 85° C., a portion of the excess AGE/isomers were stripped to give a crude GC yield of 82.1% desired hydrosilation product. GC Analysis also showed 0.14% γ-glycidoxypropyldimethyl(ethoxy) silane and 0.29% γ-glycidoxypropyltriethoxysilane. Further purification of crude γ-glycidoxypropylmethyldiethoxysilane by continuous high vacuum distillation did not separate the close-boiling exchanged side-products from desired product. Results were: γ-Glycidoxypropyltriethoxysilane was 1.3%, and γ-glycidoxypropyldimethyl(ethoxy)silane was 2.1% by GC analysis. Expected product, γ-glycidoxypropylmethyldiethoxysilane, accounted for only 94.0% of the distilled material. Redistillation in batch fashion through a fractionation column was required to provide product with greater than 97% purity by GC and combined exchanged products which were less than than 1%. Approximately 25% of the desired product was contained in less pure distillation cuts and the distillation heavies.

Example 6
Hydrosilation of Methyldiethoxysilane and Allyl Glycidyl Ether in a Production Reactor by Inverse Addition To a jacketed, glass-lined reactor, equipped with agitator, condenser and nitrogen purge, was added 6500 lb [2955 kg] (22,049 mol) of methyldiethoxysilane. CPA catalyst solution (2650 ml, 15 ppm Pt) and acetic acid promoter (6.30 lb [2.9 kg], 470 ppm) had previously been added. The reactor contents were heated to 80° C. Controlled addition of allyl glycidyl ether (6860 lb [3118 kg], 27,353 mol) to the heated mixture was then commenced. The feed controlled kettle temperature was maintained around 85° C. Again, a 20% excess of AGE is used, as competitive isomerization of AGE occurs in the presence of heat and catalyst. At the end of the AGE addition (about 7 hours), the reaction mixture was heated to 85° C. and agitated for 60 minutes. Reaction completion was determined by SiH content analysis. The lites, including excess AGE/isomers, were then stripped at reduced pressure. Crude reaction yield was 97.3% by GC analysis. Also present were the following rearranged side-products:

γ-glycidoxypropyldimethyl-(ethoxy)silane (0.10%) and γ-glycidoxypropyltriethoxysilane (0.17%). The stripped crude was then filtered and vacuum distilled (2 mm Hg) in a continuous unit, providing product of greater than 98% purity.

Comparative Example 3
Hydrosilation of Methyldiethoxysilane and Ailvy Glycidyl Ether under Continuous Conditions When the hydrosilation reaction between methyldiethoxysilane and allyl glycidyl ether was run in a continuous mode (See copending U.S. patent application Ser. No. 09/151,642, now U.S. Pat. No. 6,015,920, for continuous hydrosilation with recycling) by cofeeding allyl glycidyl ether and excess methyldiethoxysilane to a reactor and recycling the excess methyldiethoxysilane, both exchanged precursors, $Me_2(EtO)SiH$ and $(EtO)_3SiH$, were observed in the recycle stream at combined levels ranging from approximately 5% to greater than 20% of the recycled methyldiethoxysilane stream, and the crude product stream contained steadily increasing amounts of exchanged hydrosilation products as well as reaction time increased. The level of γ-glycidoxy-propyldimethylethoxysilane, for example, increased from approximately 0.5% to more than 2% relative to 70 to 78% of the expected γ-glycidoxypropylmethyldiethoxysilane.

Comparative Example 4
Hydrosilation of Methyldiethoxysilane and Vinylcyclohexene Monoxide by Prior Art Addition When the hydrosilation reaction between methyldiethoxyislane and vinylcyclohexene monoxide was run by adding the former to a 20% molar excess of the latter at 90° C., followed by a 1 hr hold at 90° C. after completion of the addition, using 10 ppm of platinum as a solution in ethanol, in the presence of aproximately 300 ppm of sodium propionate, in separate runs with and without 500 ppm of acetic acid, the alkyl/alkoxy group exhange reaction hydrosilation products were observed by GC at combined levels of 2.4–3.4% relative to the expected methyldiethoxysilane hydrosilation product at 82–84%. The acetic acid did not appreciably affect the reaction products.

Comparative Example 5
Hydrosilation of Methyldiethoxysilane with Other Olefins by Prior Art Addition A series of small hydrosilation reactions was run by adding methyldiethoxysilane to 1-octene, cyclohexene, 2,3-dimethyl-2-butene (tertiary-amylene), and eugenol. In each reaction, evidence of alkyl/alkoxy group exchange was observed by GC and confirmed by GC/MS. For 1-octene, the exchanged hydrosilation products were both observed. For cyclohexene, both exchanged precursors were observed, with only the dimethylethoxysilane hydrosilation product being observed. Results similar to those with cyclohexene were observed for tertiary-amylene and for eugenol, i.e., both precursors and the hydrosilation product of dimethylethoxysilane.

Example 7
Hydrosilation of Methyldiethoxysilane and 1-Octene by Inverse Addition The hydrosilation of methyldiethoxysilane and 1-octene as reported in Comparative Example 8 provided combined exchanged products, $Me_2(EtO)SiC_8H_{17}$, and $(EtO)_3SiC8H_{17}$, as high as 7.6% relative to 80.4% of expected $Me(EtO)_2SiC_8H_{17}$. When run by inverse addition, the combined exchanged products were 0.9%, and when run by inverse addition in the presence of acetic acid, the combined exchanged products were 0.6%, both relative to 80% of expected product.

Example 8
Hydrosilation of Methyldimethoxysilane and 1-Octene by Inverse Addition When the hydrosilation of methyldimethoxysilane and 1-octene was run under conditions of Comparative Example 5, the exchanged hydrosilation products, $Me_2(MeO)SiC_8H_{17}$ and $(MeO)_3SiC_8H_{17}$, were shown by GC analysis to be a combined 0.6% relative to 65.7% $Me(MeO)_2SiC_8H_{17}$ (0.6% normalizes to greater than 1% at 100% $Me(MeO)_2SiC_8H_{17}$). When run by inverse addition in the presence or absence of acetic acid, the combined exchange products were minimized to less than 0.2% relative to 72.9% $Me(MeO)_2SiC_8H_{17}$.

What is claimed is:

1. A method for preparing an organofunctional alkyldialkoxysilane comprising adding an olefin to a mixture of a platinum catalyst selected from the group consisting of chloroplatinic acid and platinium olefin complexes and a hydroalkyldialkoxysilane at an elevated temperature wherein formation of hydrosilation by-products arising from an alkyl/alkoxy group exchange reaction is minimized to less than one weight percent of the reaction product.

2. The method of claim 1 wherein the platinum is used at a level of 5 to 100 parts per million of metal by weight of the combined reactants, there is additionally present acetic acid used at a level of 100 to 5000 parts per million by weight of the combined reactants, the hydroalkyldialkoxysilane is selected from methyldimethoxysilane and methyldiethoxysilane, the molar ratio of olefin to hydroalkyldialkoxysilane is 1.01 to 2, the elevated reaction temperature is 50 to 150° C., and the olefin is selected from the group of allyl compounds and hydrocarbon olefins.

3. The method of claim 2 wherein the platinum is provided as a solution of chloroplatinic acid at a use level of 10 to 20 parts per million of platinum by weight of the combined reactants, acetic acid used at a level of 300 to 600 parts per million by weight of the combined reactants, the hydroalkyldialkoxysilane is methyldiethoxysilane, the molar ration of olefin to hydroalkyldialkoxysilane is 1.01 to 1.15, the elevated temperature is 75 to 105° C., the olefin is allyl glycidyl ether, and the olefin is added to the hydroalkyldialkoxysilane at reaction conditions.

4. The method of claim 1 wherein the olefin is selected from the group of vinylcyclohexene, vinylcyclohexene monoxide, 1-octene, and vinylic silanes.

5. The method of claim 1 wherein the olefin is selected from the group of cycloalkenes, non-terminal olefins, acetylenes, and acetylene derivatives.

6. The method of claim 2 further comprising a second step of purifying the product of the first step.

7. The method of claim 1 wherein the olefin is allyl glycidyl ether.

8. The method of claim 1 wherein the hydroalkyldialkoxysilane is a compound of the formula R(RO)$_2$SiH, where the R groups are each independently a lower alkyl group of one to four carbon atoms.

9. The method of claim 1 wherein the olefin is a compound of the formula $$CH_2=CR^1(CH_2)_xY,$$

where
R$^1$ is hydrogen or a lower alkyl group of one to four carbon atoms, x is an integer of 0 to 15, Y is a carbon, oxygen, nitrogen, or sulfur-bound functional group, when x is 1 or more;
    a carbon-bonded functional group wherein the bonding carbon is attached only to carbon or hydrogen atoms, provided x is 0; or
    a silicon-bonded functional group.

10. The method of claim 9 wherein the hydroalkyldialkoxysilane is a compound of the formula R(RO)$_2$SiH, where the R groups are each independently a lower alkyl group of one to four carbon atoms.

11. The method of claim 9 wherein Y is a thioether, ether, epoxide, carbamato, isocyanato, polyether, amine, or alkyl group.

12. The method of claim 9 wherein Y is glycidoxy, 1,4-epoxycyclohexyl, methacryloxy, polyetheroxy, 4-hydroxy-3-methoxyphenyl or n-pentyl group.

13. The method of claim 1 wherein the catalyst is chloroplatinic acid.

14. The method of claim 1 wherein the catalyst is a platinum-vinylsiloxane complex.

* * * * *

UNITED STATES PATENT AND TRADEMARK OFFICE
CERTIFICATE OF CORRECTION

PATENT NO. : 6,166,238
DATED : December 26, 2000
INVENTOR(S) : Filipkowski, et al.

It is certified that error appears in the above-identified patent and that said Letters Patent is hereby corrected as shown below:

Title page, Inventor, please change, "Petty E. Herbert", Should be --Herbert E. Petty--.

Signed and Sealed this

First Day of May, 2001

Attest:

NICHOLAS P. GODICI

Attesting Officer     Acting Director of the United States Patent and Trademark Office